United States Patent
Rossi

(10) Patent No.: US 7,162,297 B2
(45) Date of Patent: Jan. 9, 2007

(54) APPARATUS AND APPLICATOR PATCH FOR TRANSDERMAL SUBSTANCE DELIVERY

(76) Inventor: Elisabetta Rossi, Via Roma 12, 23873 Missaglia Lecco (IT)

( * ) Notice: Subject to any disclaimer, the term of this patent is extended or adjusted under 35 U.S.C. 154(b) by 187 days.

(21) Appl. No.: 10/381,255

(22) PCT Filed: Jul. 12, 2001

(86) PCT No.: PCT/IT01/00369

§ 371 (c)(1),
(2), (4) Date: May 8, 2003

(87) PCT Pub. No.: WO02/24274

PCT Pub. Date: Mar. 28, 2002

(65) Prior Publication Data

US 2003/0176832 A1 Sep. 18, 2003

(30) Foreign Application Priority Data

Sep. 22, 2000 (IT) .............................. FI2000A0198

(51) Int. Cl.
*A61N 1/30* (2006.01)
(52) U.S. Cl. ........................................................ 604/20
(58) Field of Classification Search .................. 604/20, 604/501; 435/173.7, 173.5, 173.6; 204/450
See application file for complete search history.

(56) References Cited

U.S. PATENT DOCUMENTS

| 5,328,452 A | 7/1994 | Sibalis |
| 5,499,967 A * | 3/1996 | Teillaud et al. ................ 604/20 |
| 5,840,057 A | 11/1998 | Aloisi |
| 5,983,134 A * | 11/1999 | Ostrow ........................ 604/20 |
| 6,022,316 A | 2/2000 | Eppstein et al. |
| 6,516,227 B1 * | 2/2003 | Meadows et al. ............. 607/46 |
| 2002/0010414 A1 * | 1/2002 | Coston et al. ................ 604/20 |

FOREIGN PATENT DOCUMENTS

WO    WO 00 27473 A    5/2000

* cited by examiner

*Primary Examiner*—Catherine S. Williams
(74) *Attorney, Agent, or Firm*—Nixon & Vanderhye

(57) ABSTRACT

Apparatus for transdermal delivery of substances contained in a carrier fluid, comprising a power supply unit which supplies an electric signal to at least two electrodes connected thereto. The electric signal is a modulated oscillating signal and the electrodes are arranged in respective patches. The apparatus may be used for the transdermal delivery of substances such as, for example, active principles for therapeutic and cosmetic use.

20 Claims, 8 Drawing Sheets

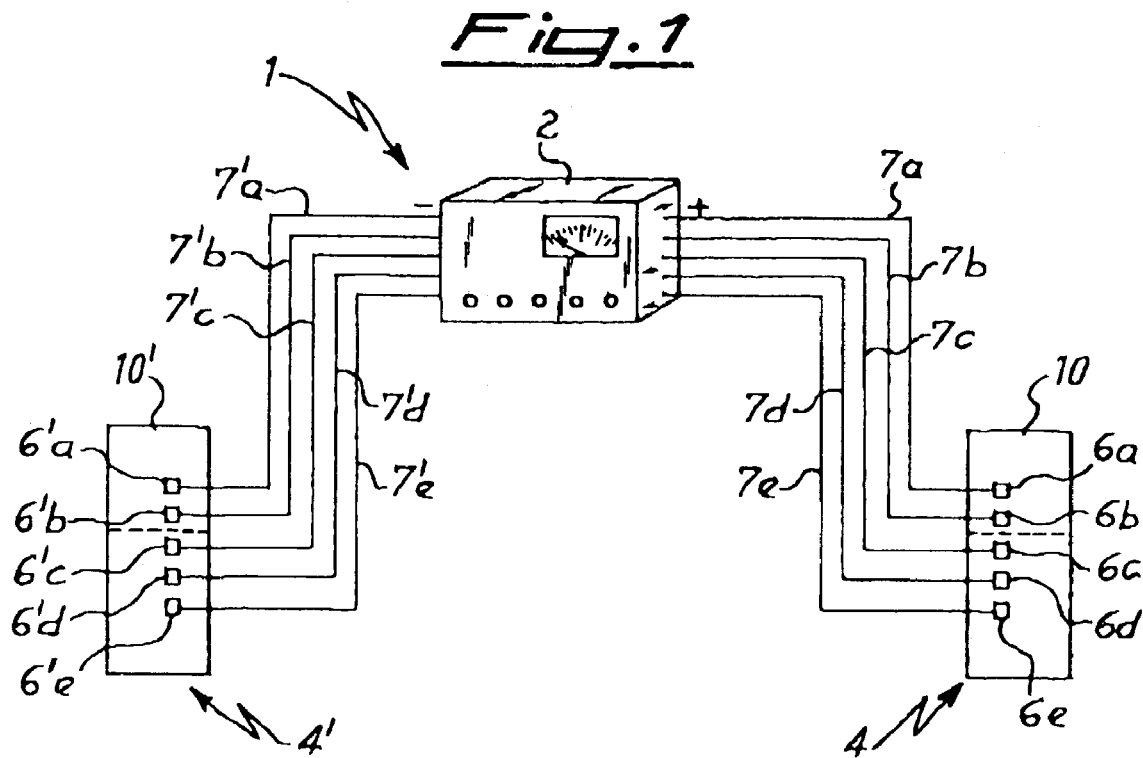
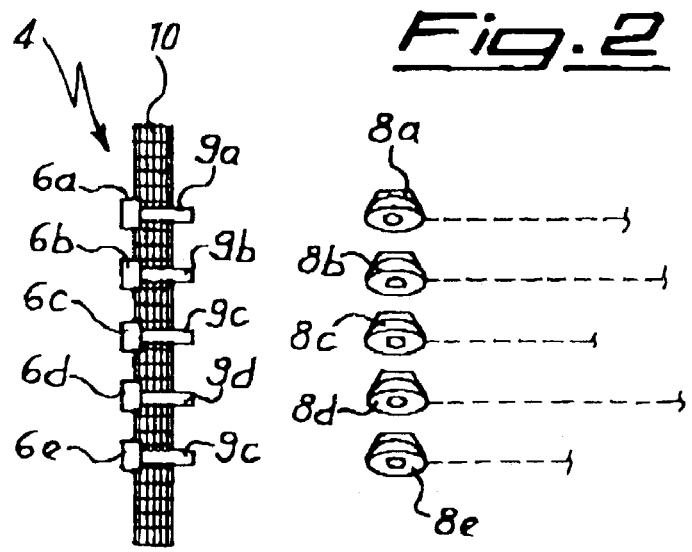

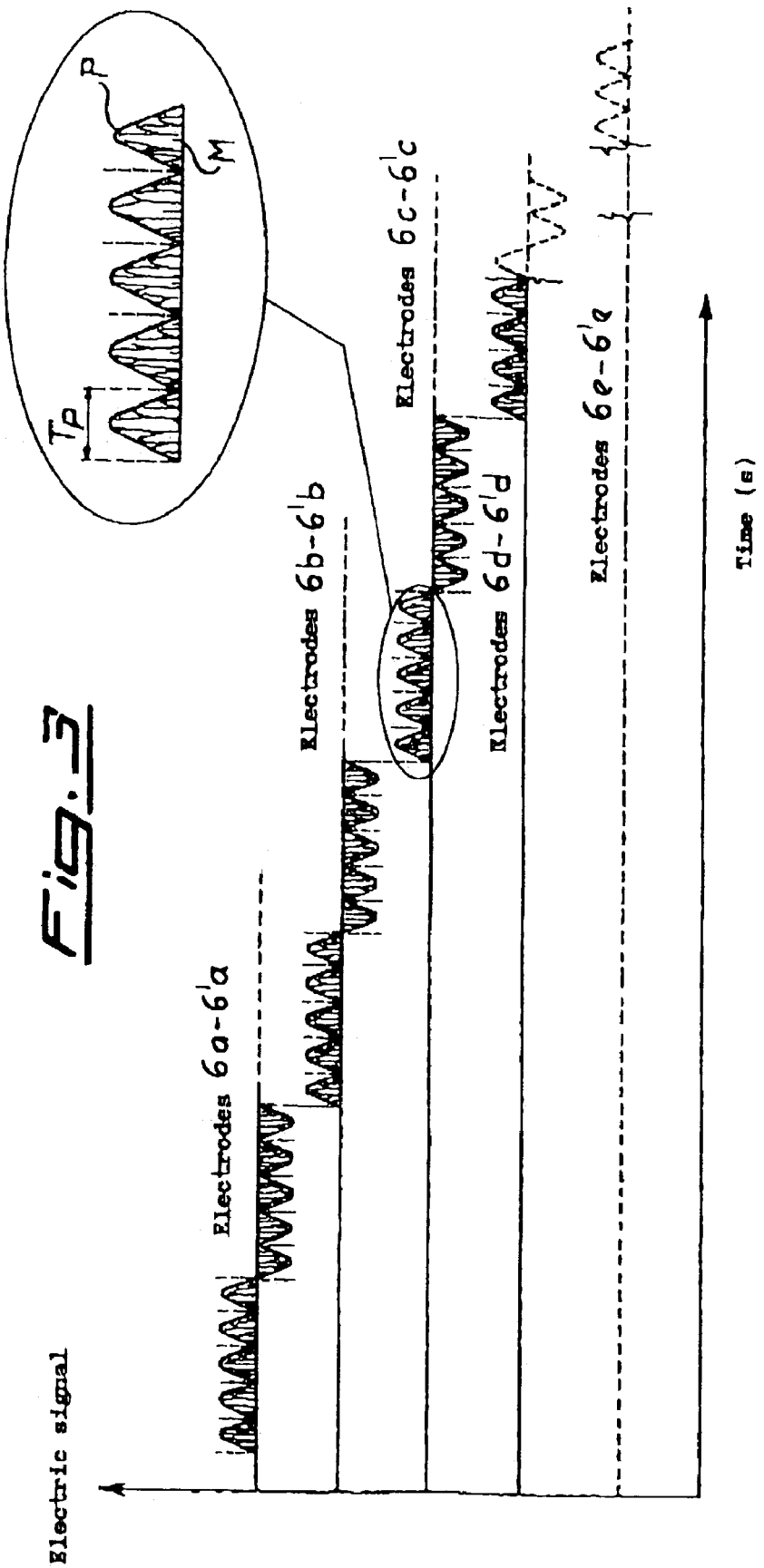

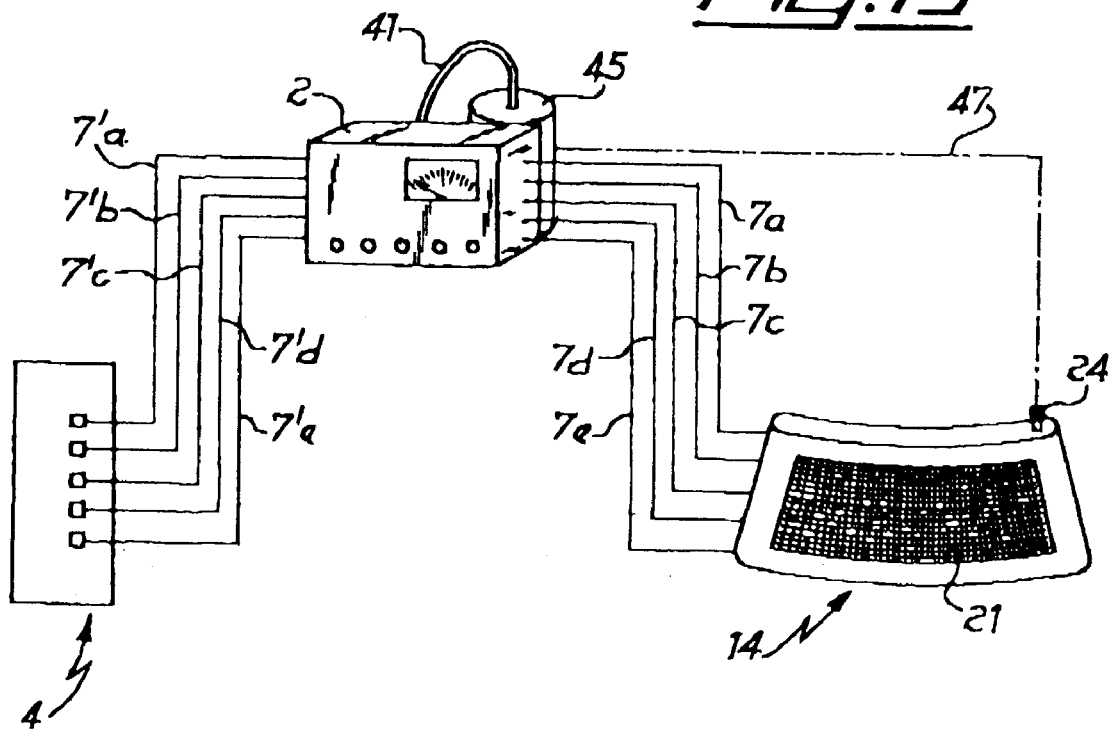
Fig.15
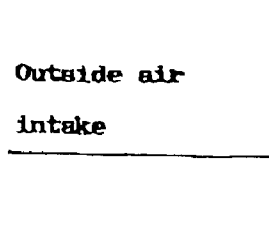
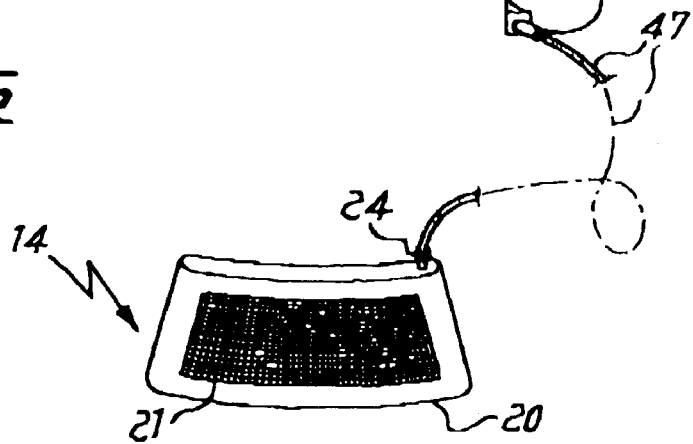
Fig.16 and distribution of electric charges is concentrated in few points, which in the case considered above are those around the contact generatrix of the rolling roller on the skin.

APPARATUS AND APPLICATOR PATCH FOR TRANSDERMAL SUBSTANCE DELIVERY

This application is the U.S. national phase of international application PCT/IT01/00369, filed Jul. 12, 2001, which designated the U.S.

The present invention relates to apparatus for delivering through the skin, substances such as drugs, salt and vitamin additives, active principles, vegetable extracts, or gases such as nitrogen, oxygen and others.

BACKGROUND OF THE INVENTION

Such apparatus are those used for iontophoresis, electro-osmosis and similar treatments, based on the migration of electric charges in order to allow penetration of substances to be administered through the skin.

The abovementioned apparatus are basically formed by a power supply unit which supplies the required voltage and electric current to electrodes connected thereto; the substances to be administered are dispersed in ionic or molecular form, in a carrier fluid contained in an applicator unit which is brought into contact with the skin of the area of the body to be treated, so as to allow the passage of the substances via electrophoretic migration.

Depending on the configuration of the applicator unit, the apparatus considered herein can be divided into two separate groups.

The first group comprises those apparatus in which said unit is essentially formed by a head, also called "dispenser", operated manually in order to perform passes along the area of the body to be treated; according to one embodiment, the applicator head is provided with a roller, above which a container with the carrier fluid is arranged upside-down.

Said fluid moves down from the container and licks an electrode in such a way that the ion substances to be administered and dispersed therein, can pass through the skin, as a result of the rolling of the roller which spreads the carrier fluid over the patient's skin with each pass of the applicator head; an example of this state of the art is described in Italian patent application No. FI99A00055 of Mar. 22, 1999.

The apparatus of the second group referred to above, are those wherein the applicator unit is essentially a compress, also called a "patch", which is placed on the area of the body to be treated.

Examples of these apparatus are described in several documents and publications, including European patent application No. 292,930 and U.S. Pat. No. 5,084,008.

In these cases the patch has the function of a container for the carrier fluid and has a wall permeable to the substances to be administered, which can be formed by means of an osmotic membrane, a flexible mesh, or the like; an electrode associated with the container causes the migration, on an ionic level, of said substances, which for this purpose pass through the permeable wall placed on the skin of the area of the body to be treated.

The electrode of these known apparatus is usually a mesh or a metallic plate present in the patch, but can also be a wall of the latter, indeed, the container which forms the patches is generally rigid, so that by forming or lining one or more of its walls with metallic material, they can act as electrodes.

However, both groups of apparatus referred to above have intrinsic limitations in their operation, which make them unsuitable for certain applications.

Indeed, the apparatus with dispenser operated manually allow substances to be delivered deeply because the flow of the electric charges is concentrated in few points, which in the case considered above are those around the contact generatrix of the rolling roller on the skin.

However, since the dispenser must be operated manually, these apparatus require the continuous presence of an operator: therefore they are not very advantageous in terms of costs since the staff of hospitals, clinics and the like must attend to the treatment sessions for all duration thereof.

It should also be borne in mind that, for the same reasons, it is not possible to treat several parts of the body at the same time, nor several patients at the same time (one operator could not be able handle two dispensers at the same time); if, in addition to this, it is considered that human intervention is inevitably a source of lack of uniformity in the treatments performed by different operators (an other factors being equal), it can be understood how this type of apparatus has limitations either from the point of view of service management (in hospitals, outpatients' departments etc.), and from the point of view of the regularity of the treatments performed.

On the contrary, in the case of apparatus with an applicator patch these limitations are overcome: indeed, once the patch has been positioned on the are of the body to be treated and connected to the power supply unit programmed for the treatment, there is an fact no more need for any action by an operator.

However, this type of apparatus has some problems from the point of view of substances delivery.

Indeed, these apparatus do not allow deeply located tissues to be reached effectively; this is due to the fact that in order to obtain certain levels of penetration, excessively high voltage and/or current values would have to be applied to the electrodes.

SUMMARY OF THE INVENTION

The present invention intends to remedy this state of the art; namely it has the object of providing an apparatus for iontophoresis, electro-osmosis and similar treatments, with such structural and functional features as not to require continuous manual intervention by an operator and allow the deep and effective administration of any type of substance.

This object is achieved by an apparatus whose characterizing features are set out in the claims which will follow.

BRIEF DESCRIPTION OF THE DRAWINGS

The invention will be better understood in the light of the description given hereinafter, of a non-limiting embodiment thereof and some variations, shown in the accompanying drawings wherein:

FIG. 1 is a schematic representation of an embodiment as a whole, of an apparatus according to the invention, FIG. 2 is a cross-sectional view of an applicator patch of the apparatus in FIG. 1;

FIG. 3 is a graph showing the trend over time of the current supplied to the electrodes of the above apparatus;

FIGS. 15 and 16 show a power supply unit for an apparatus according to the invention, with a pump system for the carrier fluid.

DETAILED DESCRIPTION OF PREFERRED EMBODIMENTS

Figure 4:
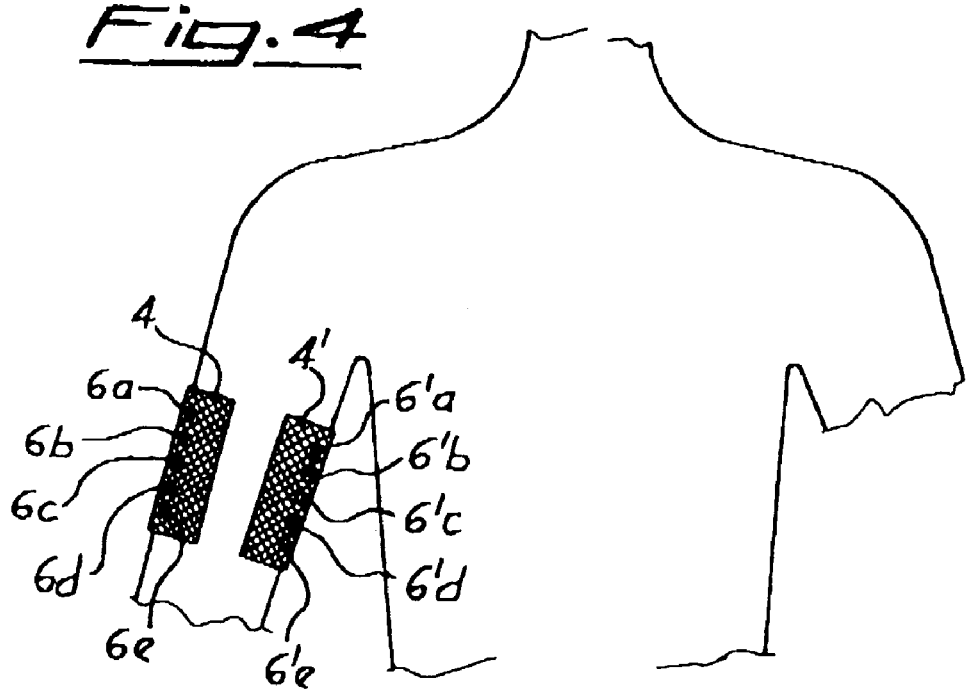
FIG. 4 shows in detail an application of the apparatus of FIG. 1.

With reference to the drawings, 1 denotes in its entirety all apparatus according to the invention which comprises a power supply unit 2 which supplies the electrical energy required for the treatment to be carried out; said unit can be connected to the public mains network or can have batteries for independent operation.

The apparatus 1 further comprises two patches 4 and 4' in which two series of electrodes 6a–6e and 6'a–6'e are respectively arranged; each of said electrodes is connected to the power supply unit 2 by means of corresponding electric wires 7a–7e and 7'a–7'e.

Each of the electrodes 6a–6e, 6'a–6'e is formed by a conductive metallic plate, preferably having a surface area of between 0.5 and 5 $cm^2$.

The removable electrical connection of the wires 7a–7c, 7'a–7'e to the respective electrodes can be achieved in any appropriate way, for example with clips or with studs 8a–8e of the press button type (in FIG. 1 only those associated with the cables 7a–7e have been shown, while those of the cables 7'a–7'e, which are identical, have not been shown in the drawings for sake of simplicity) commonly called "snap-engagement studs", snap-engaged onto pins 9a–9e of the electrodes projecting from the patch.

As will be seen better hereinafter, the patches 4, 4' can be designed in various ways; in this example each of them is obtained with a strip or band 10, 10' of biacompatible material (for example fabric, a polymer layer or a layer of material of any another kind used for cosmetic and medical applications) in order to avoid problems of skin allergies, irritations etc., where the electrodes are arranged on the side thereof directed towards the part of the body to be treated when the patch is applied.

According to the invention, the patches 4, 4' are used by placing between them the part of the body to be treated, over which the gel containing the substances to be delivered has been spread beforehand (cf. FIG. 4).

Furthermore, in this case the patches 4, 4' are held firmly in position by means of normal adhesive tape or other equivalent system; of course, other fixing solutions are also possible, according to the different configuration of the patches which depends, among other things, on the part of the body for which they are intended.

The power supply unit 2 is essentially a generator provided with electronic components known per se, which allows to supply a modulated electric signal, preferably a tension signal, to the electrodes 6a–6'a, 6b–6'b, 6c–6'c, 6d–6'd, 6e–6'e, in an independent manner.

In particular, as can be seen from FIG. 3 in which the trend of the voltage applied to the electrodes is shown, the signal M is of the oscillating type and is amplitude-modulated with a periodic pulsating, triangular or sawtooth profile P; the pulsations of this profile have a duration Tp which is variable preferably between 0.5 and 10 s, while the modulated wave of the signal M has a frequency of between 50 and 3,000 Hz.

In addition to this, the polarity of the pairs of electrodes which are supplied one after the other, is reversed after the first series of pulsations of the profile P (5 in the graph in FIG. 3).

The signal frequency and amplitude values, as well as the profile of the modulation carrier, are variable depending on various factors such as the type of substances to be delivered the part of the body concerned by the treatment, the depth, with respect to the skin of the tissue to be reached, the characteristics of the patient and other factors.

These values can be preset in each individual case on the power supply unit, which is provided with means for regulating the voltage, the frequency and the current; for this purpose, tests may be carried out on the patient beforehand or medical tables obtained experimentally may be used.

It should nonetheless be pointed out that the voltage and current values for the treatments performed with the apparatus according to the invention, fall within the ranges normally used for iontophoresis, electro-osmosis and similar traditional treatments.

To sum up, in the functioning of this example of the invention, the modulated electric signal is initially applied to the first pair of electrodes 6a–6'a, carrying out a series of n pulsations (5 in the example considered) of the profile P, during which the electrode 6a has a potential higher than that of the electrode 6'a; after this polarity of the latter electrode is switched with the polarity of the other electrode and a new series of n pulsations is performed. It can be noted that the values of the voltage applied to the electrodes of each pair can be of the same or mutually opposed sign.

Once this operating cycle is finished, the next electrodes 6b–6'b (6c–6'c, 6d–6'd etc.) are supplied using the same procedure and so on until completion of all the N pairs of electrodes; afterwards the cycle is restarted from the first pair of electrodes.

From the above description it is possible to understand how the apparatus according to the invention achieves the object defined initially.

In the first place, it is clear that since the apparatus is of the type comprising applicator patches, it does not require the continuous presence of staff persons to carry out the treatments; indeed, once the patient has been prepared with the patches and the electrodes have been connected to the power supply unit as explained above, the apparatus is capable of performing the desired treatment independently.

In this connection it just has to be added that the power supply unit is provided with means known per se in order to programme the functioning thereof, according to the operating cycle which is set by the operator.

The apparatus according to the present invention does not have, however, the limitations which distinguish conventional apparatus provided with applicator patches.

Indeed, the use of a modulated periodic electric signal provides for an effective passage of the ionic substances through the skin, so as to reach in fact any tissue located at any depth; for this purpose it is sufficient to regulate the modulation parameters of the signal, i.e. amplitude, frequency and waveform.

This effect is enhanced by the fact that in the apparatus according to the invention the electrodes preferably have a limited surface area, such that the substances to be delivered migrate in a concentrated manner in the region of said electrodes; in practice, this allows to reproduce a situation similar to that of the contact between the generatrix of the roller and the skin, occurring in the known apparatus with a roller dispenser.

Moreover, the periodic reversal of the voltage applied to the electrodes allows ion substances with positive and negative polarity contained in the same gel, to be delivered, thereby widing significantly the range of treatments which can be performed with the apparatus and the effectiveness thereof; it can be noted that this result is obtained without having to remove the patches for reversing the arrangement of the electrodes, since the reversal in polarity is carried out by the power supply unit itself.

In this context it should also be pointed out that the transient state which is produced with the alternation in the polarity of the electrodes, prevents the formation of static conditions in the body which might have a negative effect on the passage of the substances to be delivered.

Lastly, the activation in succession of the electrodes arranged on different parts of the body to be treated, also allows the effect of the subsequent passes of the roller dispenser to be reproduced without, however, requiring any manual intervention: from this fact it can be appreciated that the apparatus according to the invention solves all the problems of the general state of the art, formed both by the apparatus comprising a manually controlled operating head and by apparatus comprising patches.

It should be noted that the frequencies used to supply the electrodes in the apparatus according to the invention are very different from the frequencies mentioned in European patent application No. 292,930 mentioned above; indeed, in said document the voltage or current pulsations occur at time intervals which vary from a few minutes to a few hours.

This is due to the fact that this state of the art relates to the delivery of substances into the blood system and not into muscle, skin or bone tissues, as in this case; with the present invention, therefore, it is possible to achieve the intracellular metabolisation of the substances in the target tissue.

Naturally, variations of the invention with respect to the example thereof given above are possible.

In the first place it should be pointed out how the waveforms which can be used to modulate the electric signal applied to the electrodes may be different from the sawtooth profile shown in the drawings; for example, it is possible to have modulated electric signals with a carrier having a square half-wave (therefore leaving an interval between one series of pulses and the next) or a round or other form of half-wave.

It should also be considered that the modulated electric signal can be applied simultaneously to all the pairs of electrodes, i.e. not only in succession one after the other as in the example given above.

Another important aspect to be emphasized is that the number of applicator patches connected to the power supply unit, can be less or more than the two considered.

Figure 5:
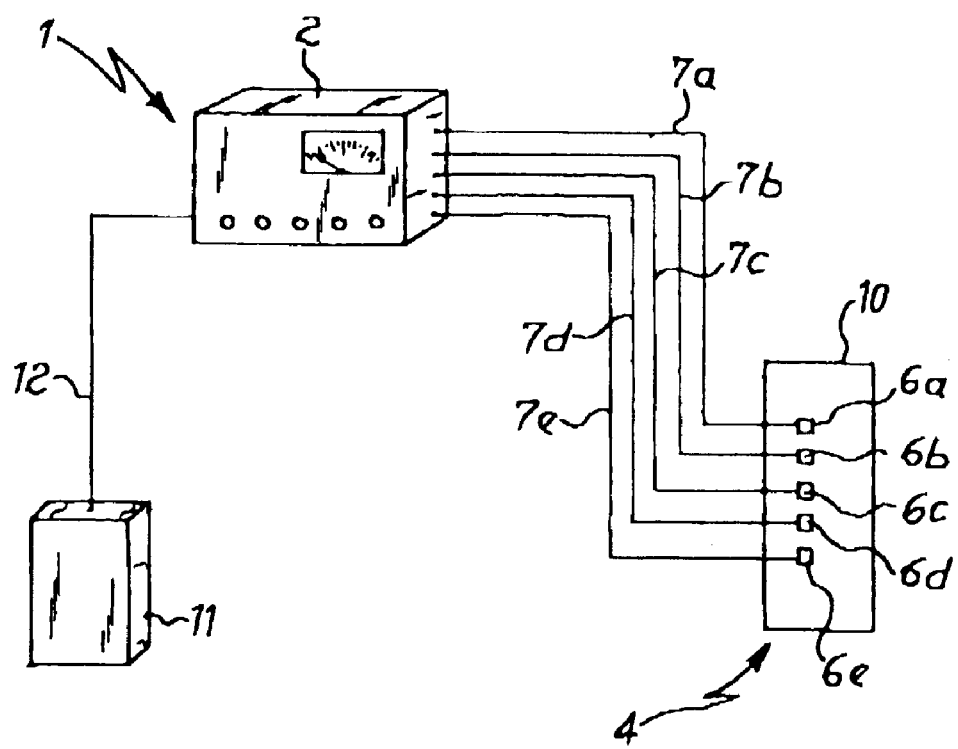
FIG. 5 shows a variation of the apparatus in FIG. 1.

For this purpose, reference is made to FIG. 5 where it can be seen that it is possible to replace one of the patches and the associated electrodes, with an earth 11 connected to the power supply unit 2 by means of a cable 12; such a solution can be used in applications where the conditions do not require the use of a second patch.

Likewise, there may instead be cases where there are four or more patches; i.e. it is possible to imagine an apparatus obtained by subdividing the patches 4, 4', like it is shown with the broken line in each of the patches of FIG. 1.

Two patches would therefore be obtained from each of them, one with two electrodes and the other with three, said patches being connected to the cables 7a–7e, 7'a–7'e and supplied by the unit 2.

Various alternatives as regards the applicator patches are also possible with respect to what has been disclosed above.

In this connection it should be pointed out that an important aspect relating to the applicator patch, is its capacity to adapt to the part of the body to be treated; indeed this allows optimum positioning of the electrodes with respect to the skin, so as to ensure a more effective flow of the current from the electrodes to the tissues.

It can therefore be understood that the patch must be structurally flexible so as to allow it to be placed on the skin in a uniform manner, with the electrodes arranged in the correct position.

In order to improve this effect the patch may moreover be anatomically shaped, depending on the area of the body for which it is intended; in other words, the band 10 seen above is suitable for wrapping around the arm as shown in FIG. 4, but cannot be used, for example, for applications in the cervical area.

Naturally, in said area it is more suitable to have a collar-shaped patch.

Further constructional variations of said patch may also be derived from the type of treatment to be performed; for instance, the band 10 of the preceding example is suitable for applications wherein the substance or the active principle to be delivered are contained in a gel or a fluid with a high viscosity.

However, in the case where the substance or the active principle are dispersed in a liquid, it is clear that the abovementioned band cannot be of any use and the applicator patch must instead have the features of a container.

Figure 6:
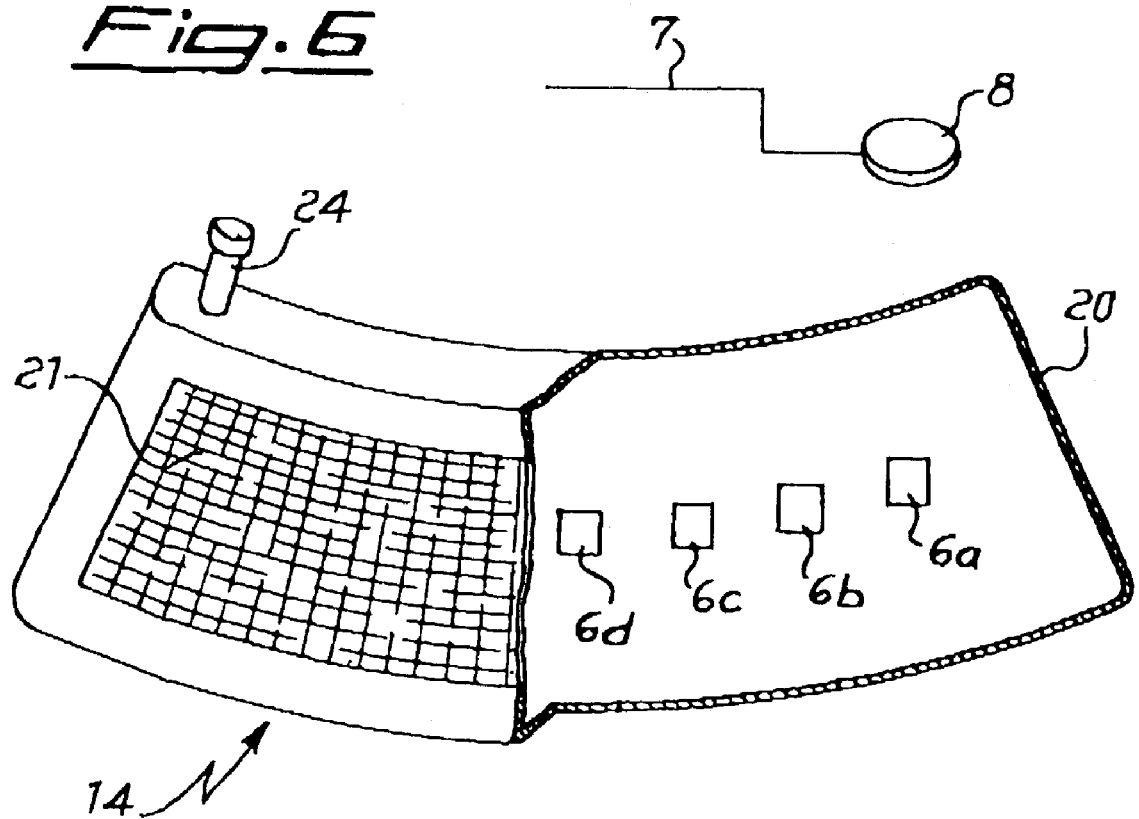
FIGS. 6 to 14 show respective possible embodiments of applicator patches for the apparatus according to the invention.
Figure 7:
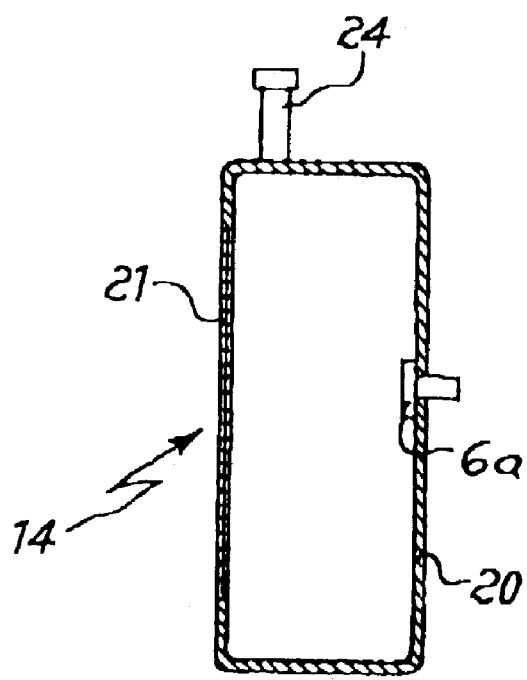

In order to better appreciate the abovementioned variations, reference can be made to FIGS. 6–14 where some examples of applicator patches are shown, FIGS. 6 and 7 also showing the internal structure thereof.

As can be seen, in this case the applicator patch 14 comprises, instead of the band 10, a closed wrapping 20 which can contain liquids inside it; for this purpose the wrapping 20 is made of any flexible, impermeable, and preferably biocompatible material, with the exception of one wall 21 thereof.

This wall must indeed allow the passage of the substances to be delivered and therefore must be permeable with respect thereto; in order to obtain this result, various solutions are possible depending on the viscosity of the fluid.

For example, the wall may be formed by an osmotic membrane or by a sheet of perforated rubber, or also by a mesh as in the drawing in FIGS. 6 and 7.

In this latter case the wall 21 is a perforated meshwork which has holes of approximately 0.1–0.5 cm and is formed by synthetic or natural threads of 1–1.5 mm; the electrodes 6a, 6b, 6c, 6d, 6e, which can be connected to the power supply unit in a similar way to that already seen above, are located on the opposite wall of the wrapping 20 to the perforated wall 21.

Lastly, there is an inlet 24 on the wrapping 20 of the patch 14, through which the liquid containing the substances to be administered is introduced (by means of a syringe, a pump or other method).

As can be understood, the use of this patch for a treatment session occurs in a similar way to the above explanation, to which reference is made for the sake of brevity.

It needs only to be pointed out that this applies also to the other possible configurations of the wrapping 20 shown in FIGS. 8 to 13 where, for the sake of simplicity the same numbering has been retained for the elements structurally or functionally equivalents to those already described; as can be seen, each of said configurations is anatomically shaped to the part of the body for which it is intended.

Figure 8:
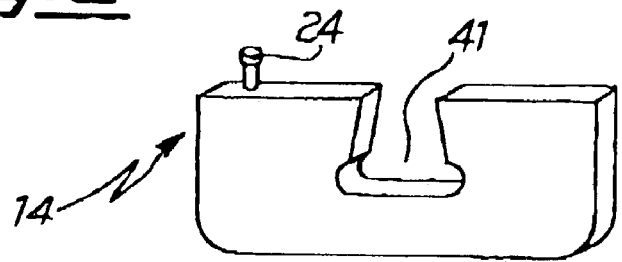

From a brief overview of these embodiments, it can be observed that the patch 14 in FIG. 8 is used for treatment of the face and is so shaped as to cover the cheeks up to the cheekbones, leaving the nose, uncovered and passing through the central slit 41.

Figure 9:
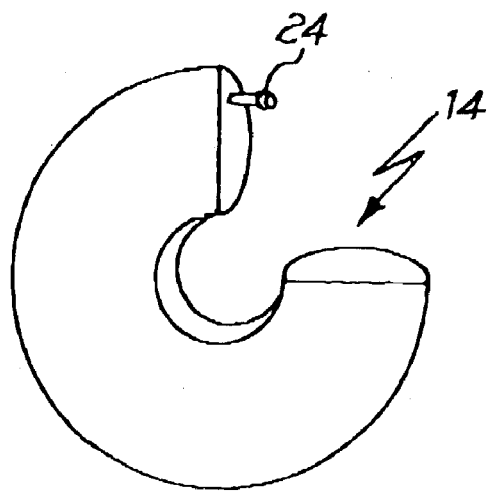
Figure 10:
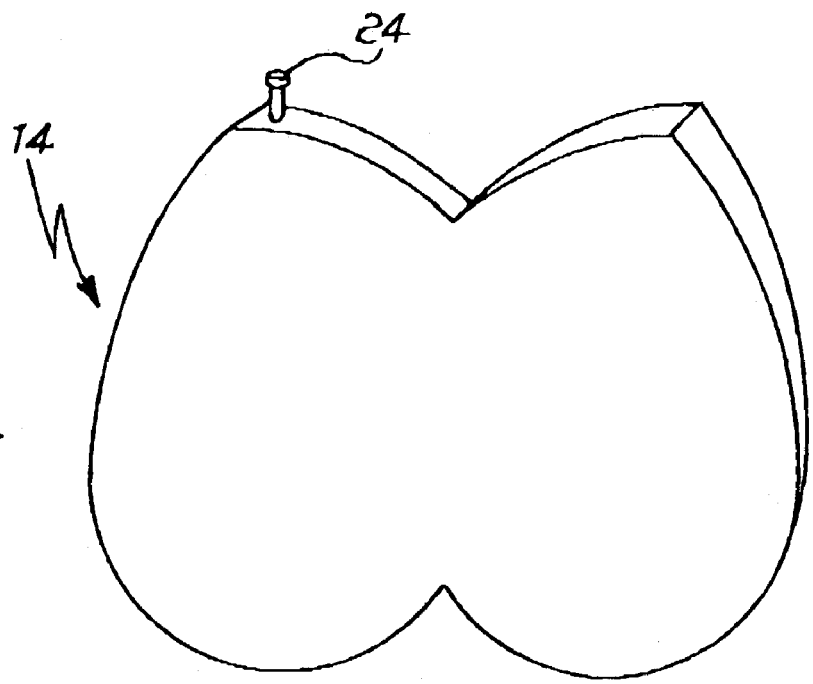
Figure 11:
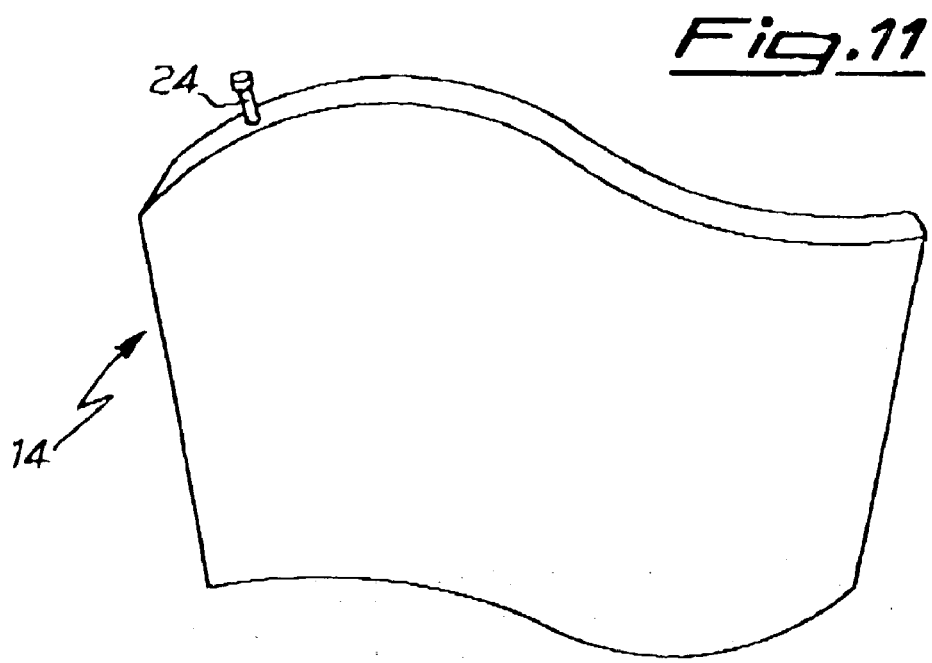

The patch in FIG. 9 is instead intended for the treatment of the breast and has a slightly conical shape; the patch in FIG. 10 serves for applications on the glutel, while the patch in FIG. 11 is intended for treatment of the thighs.

Figure 12:
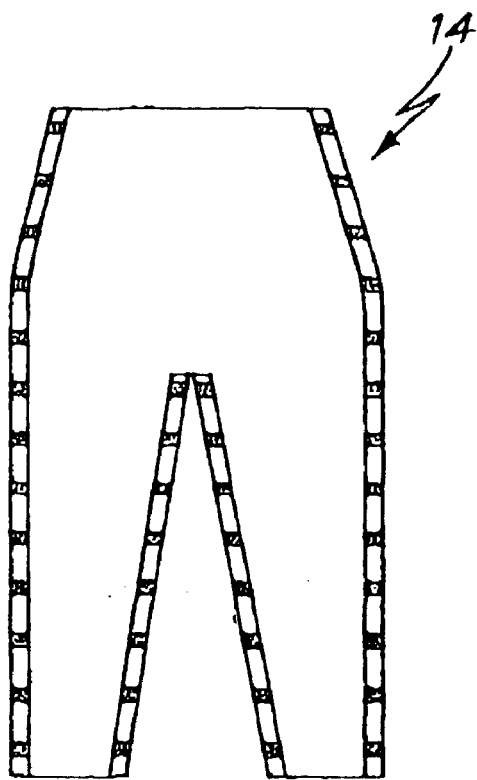
Figure 13:
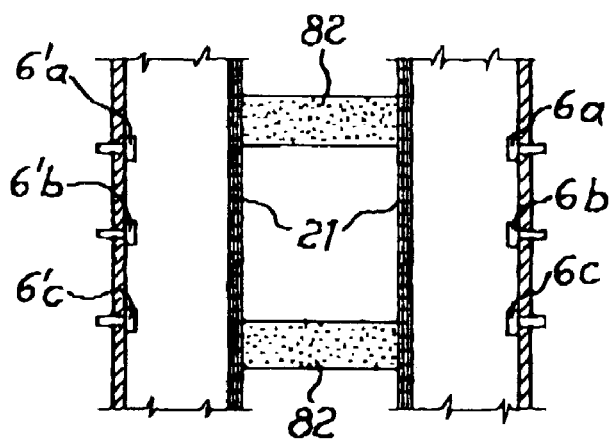

Lastly, the shape shown in FIG. 12 is obtained by connecting the front part and the rear part of a pair of trousers, said parts being respectively intended to act as a wrapping for the gel (see FIG. 13) together with the permeable wall 21 through which the substances filter; lateral strips 82 which can be of elastic, Velcro® or other material, connect the front and rear trouser parts.

The patches may also be provided with belts or the like in order to fix them to the patient's body, in the place of the medical plaster considered above; naturally, said belts may also be provided with means for fastening them, such as Velcro® strips, buckles and whatever else.

Figure 14:
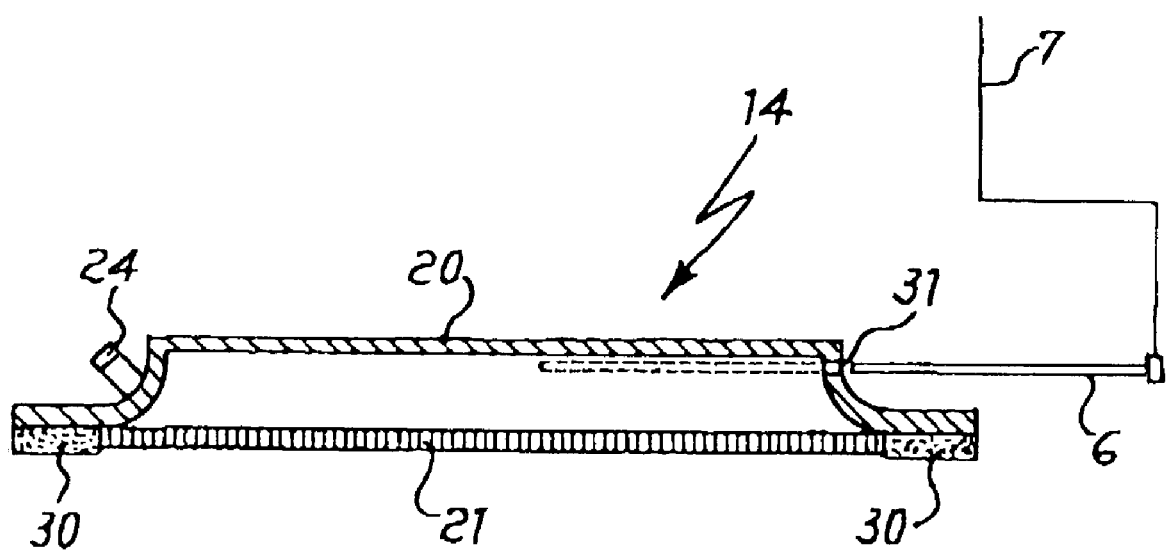

In this connection it should be considered the possibility of providing a self-adhesive patch, which can be applied in a similar way to a large plaster; this possibility is shown (in cross-section) in FIG. 14 in relation to a patch of the wrapping type, but obviously it can also be extended to patches of the band type.

In short, this example differs for the preceding ones in that an adhesive edge 30 is provided around the permeable wall 21 likewise a frame, and the electrodes 6 are formed by respective plugs inserted into the wrapping 20 through respective openings 31 (in FIG. 14 only one of these plugs has been shown but there are more of them, the as in the case of the electrodes in the preceding examples).

Owing to the adhesive edge, such a patch can be applied on the patient in the manner of a large plaster, therefore being practical and suitable for disposable uses.

Last, it should be pointed out how, from the functional point of view, the apparatus according to this invention is advantageously flexible.

Indeed, as already explained the patches can be replaced in each case in such a way that they may basically be regarded as spare parts of the apparatus.

For this purpose the patches may therefore be produced and distributed in sterile packages, like patches for medical use to be opened at the moment when the treatment is performed; after use the patches will preferably be thrown away but it should not be excluded that, in some cases, they can be kept in an appropriate manner for other applications on the same patient.

For this purpose in a preferred embodiment the band or the wrapping, depending on the type of configuration used for the patch, may be produced industrially by applying on them or filling them with freeze-dried or gelified material to be hydrated, said material containing the substances to be delivered.

The patches packaged in this way will be advantageously ready for use so that once opened, it is sufficient to moisten the freeze-dried or gelified material for applying said patches directly on the part of the body to be treated; in this manner it is possible to avoid spreading the gel on the skin beforehand or having to fill the wrapping first, depending on the situation, thereby reducing the time needed for each session to be carried out.

Lastly, the possibility that the power supply unit may be provided with other functions, in addition to that of supplying energy to the electrodes, should also be considered.

Said possibility is shown in FIGS. 15 and 16 (where the parts already seen have the same numbering), referring to an apparatus according to the invention in which the power supply unit 2 also includes a compressor 40 connected by a delivery pipe 41 to a reservoir 45, associated with the unit 2.

This reservoir has the function of a container for accumulating the carrier fluid and has a capacity approximately 3–10 times greater than that of a patch 14 of the wrapping type already explained above, to which it is connected by means of a second pipe 47.

This variation of the invention allows the patch of the wrapping type 14 to be filled quickly, which operation would otherwise have to be done using syringes or other equivalent systems.

In order to perform filling of the patch, the compressor 40 is activated thereby compressing air coming from the environment outside the unit 2, to values slightly higher than atmospheric pressure; the compressed air then passes into the delivery pipe 41 and reaches the reservoir 45.

Said reservoir is therefore pressurized in such a way that the carrier fluid inside it is pushed by the pressure along the second pipe 47, and enters the patch 14 through the inlet 24 provided thereon.

A solution like that described above has the advantage that the carrier fluid does not come into contact with the components of the compressor 40, thereby avoiding that the latter be cleaned every time it is used.

It is also clear that it is possible to use the same reservoir 45 to fill several patches in succession, or several reservoirs 45 containing respective fluids which are connected to the compressor in each case.

These and other possible variations nonetheless fall within the scope of the following claims.

The invention claimed is:

1. Apparatus for transdermal delivery of a substance contained in a carrier fluid, comprising a power supply unit which supplies a modulated oscillating electric signal to electrodes connected thereto, wherein at least two of said electrodes are arranged in respective patches with electrodes on a same patch having the same polarity, and wherein each patch comprises a flexible, closed, wrapping which can be filled with a fluid carrying the substance to be delivered and has a wall which is permeable to said substance.

2. Apparatus according to claim 1, wherein said electric signal has an oscillating frequency of between 50 and 3,000 Hz.

3. Apparatus according to claim 2, wherein the oscillating electric signal is amplitude modulated with a periodic pulsating profile.

4. Apparatus according to claim 3, wherein the pulsating profile for the modulation of the signal has a pulsation duration (Tp) of between 0.5 and 10 seconds.

5. Apparatus according to claim 4, wherein the polarity of the signal applied to an electrode is reversed after a predefined time interval.

6. Apparatus according to claim 1, wherein said power supply unit supplies said oscillating electric signal in temporal succession to a plurality of electrodes connected thereto.

7. Apparatus according to claim 1, wherein each of said at electrodes has a surface area of between 0.5 and 5 $cm^2$.

8. Apparatus according to claim 1, wherein the patch is to be applied onto a part of the body to be treated.

9. Apparatus according to claim 8, wherein the patch comprises a band of flexible textile and/or polymer material onto which the electrodes are applied.

10. Apparatus according to claim 9, wherein the electrodes are removably connected, by means of respective fastenings, to electric wires for connection to the power supply unit.

11. Apparatus according to claim 1, wherein the wall permeable to the substance to be delivered is formed by means of one or more systems selected from a perforated meshwork, an osmotic membrane, and a sheet with holes passing there through.

12. Apparatus according to claim 1, comprising a compressor associated with the power supply unit, whose delivery is connected to a reservoir communicating with the wrapping of the patch.

13. Patch for an apparatus according to claim 1, comprising a flexible band of textile and/or polymer material, with a plurality of electrodes associated thereto, said electrodes having respective pins which project from the band and can be connected to a unit supplying an electric signal.

14. Patch for an apparatus according to claim 1, comprising a substantially closed, flexible, wrapping with a wall which is permeable to the substance to be delivered.

15. Patch according to claim 14, comprising a plurality of electrodes fixed to the wrapping in a position opposite to said permeable wall.

16. Patch according to claim 14, comprising a plurality of openings passing through the wrapping for the insertion of plugs.

17. Patch according to claim 13, wherein an adhesive edge is present along the periphery of the band or of the permeable wall.

18. Patch according to claim 13, wherein the band or the wrapping provided with belts or other securing means for the attachment to a part of the body.

19. Patch according to claim 13, wherein the band or the wrapping have an anatomical configuration corresponding to the part of the body for which they intended.

20. Patch according to claim 13, wherein freeze-dried or gelified material is applied on the band or on the wrapping.

* * * * *